United States Patent [19]

Christoudias

[11] Patent Number: 4,545,373

[45] Date of Patent: Oct. 8, 1985

[54] SILASTIC TUBE RELAY ROD

[76] Inventor: George C. Christoudias, 331 River Rd., New Milford, N.J. 07646

[21] Appl. No.: 491,587

[22] Filed: May 4, 1983

[51] Int. Cl.$^4$ .............................................. A61B 17/00
[52] U.S. Cl. .............................................. 128/303 R
[58] Field of Search .............. 128/303 R, 335, 200.26, 128/657, 772; 3/1.4

[56] References Cited

U.S. PATENT DOCUMENTS

| 2,170,693 | 8/1939 | Ovington | 128/335 |
| 2,657,691 | 11/1953 | Nordstrom, Jr. | 128/303 R |
| 2,788,787 | 4/1957 | Trace | 128/303 R |
| 2,803,253 | 8/1957 | Campbell, III | 128/327 |
| 3,999,551 | 12/1976 | Spitz et al. | 128/303 R |
| 4,244,370 | 1/1981 | Furlow et al. | 128/303 R |
| 4,372,302 | 2/1983 | Akerlund | 128/303 R |
| 4,418,693 | 12/1983 | Le Veen et al. | 128/303 R |

FOREIGN PATENT DOCUMENTS

| 2542241 | 4/1976 | Fed. Rep. of Germany | 128/335 |
| 2815614 | 10/1978 | Fed. Rep. of Germany | 128/303 R |
| 1546172 | 5/1979 | United Kingdom | 128/303 R |

OTHER PUBLICATIONS

Surgery, vol. 28, Oct. 1950, pp. 749–750, John L. Madden, M.D., "Malleable Ligature Carrier".
Surgery, vol. 27, Feb. 1950, pp. 280–281, Jack W. Cole, M.D. et al., "A Polyethylene Rod Vein Stripper".
Current Problems in Surgery, vol. XVI, No. 2, Feb. 1979, Ascites: Its Correction by Peritoneovenous Shunting, by Harry LeVeen, M.D., Simon Wapnick, M.D., Carlos Diaz, M.D., Saul Grosberg, M.D., and Michael Kinney, M.D.
Peritoneovenous Shunting for Ascites, by Harry H. LeVeen, M.D., George Christoudias, M.D., Moon Ip, M.D., Richard Luft, M.D., Gerald Falk, M.S., Saul Grosberg, M.D., Annals of Surgery, Oct. 1974, vol. 180, No. 4, pp. 580–591.

Primary Examiner—Stephen C. Pellegrino
Assistant Examiner—Gene B. Kartchner
Attorney, Agent, or Firm—Martha G. Pugh

[57] ABSTRACT

The invention relates to a technique and instrument comprising a relay rod for performing subcutaneous placement of silastic tubing or vascular grafts from incisions in different parts of the body, more particularly, peritoneovenous shunts or peripheral arterial by-pass. The relay rod, which is of rigid non-toxic material, comprises a receptor bore near the tip of its head for threading through the end of the silastic tube or vascular graft. A pair of longitudinally-extended grooves, distal to the receptor bore, accommodate the end portions of the silastic tube or vascular graft, which are secured in place parallel to the rod axis by a pair of ties which rest in circumferential grooves near the upper and lower ends of the longitudinal grooves. The distal end-portion of the rod comprises a shaft and a striated handle to facilitate gripping. The relay rod, with the silastic tube or the vascular graft secured in place thereon, is passed subcutaneously between incisions in different parts of the body. When the traverse has been completed, the ties are removed, allowing the silastic tube or vascular graft to be removed from the relay rod, and the latter to be removed from the subcutaneous tunnel.

10 Claims, 11 Drawing Figures

SILASTIC TUBE RELAY ROD

BACKGROUND OF THE INVENTION

This invention relates in general to techniques and apparatus for passing a silastic tube or vascular graft through a living body subcutaneously, more particularly when performing a peritoneovenous shunt or an arterial bypass.

Such techniques are used primarily for the diversion into the venous system of ascitic fluid, which collects in the peritoneal cavity from the liver capillaries during certain conditions associated with cirrosis of the liver or ascites that developes secondary to abdominal malignancy. The accumulation of excessive fluid in the peritoneal cavity causes increased intra-abdominal pressure which may restrict the respiratory function, and also causes severe protein and caloric malnutrition which interferes with the appetite, and depletes the nutritional state of the body, lowering the resistance to infection and possibly causing peritonitis. Such techniques are also used for the placement of vascular graft between two patent areas of the arterial system to bypass an occluded area of an artery such as a femoropopliteal bypass from the common femoral artery to the popliteal artery to bypass an occluded superficial femoral artery.

In order to relieve the accumulation of excessive ascitic fluid in the peritoneal cavity and the pathophysiological changes which it brings about, and to partially compensate for the severe protein and caloric malnutrition which accompanies such accumulations, techniques have been devised in the prior art for diverting the ascitic fluid into the venous system. These are described in detail in a paper entitled *Peritoneovenous Shunting for Ascites* by Harry H. LeVeen, M.D., George Christoudias, M.D., Moon IP, M.D., Richard Luft, M.D., Gerald Falk, M.S., Saul Grosberg, M.D., Annals of Surgery, October 1974, Vol. 180, No. 4, Pages 580–591, Copyright by J. B. Lippincott Co., 1974, and a booklet entitled *Current Problems in Surgery*, Vol. XVI, No. 2, February 1979, *Ascites: Its Correction by Peritoneovenous Shunting*, by Harry H. LeVeen, M.D., Simon Wapnick, M.D., Carlos Diaz, M.D., Saul Grosberg, M.D, and Michael Kinney, M.D., published by Year Book Medical Publishers, Inc., Chicago, Ill., © Copyright 1979.

The techniques for a peritoneovenous shunt there described involve the passage subcutaneously from an abdominal incision to an incision in the neck of a slender bronchial alligator or rectal biopsy forceps. A long line of suture is attached to the forceps and pulled from the neck incision to the abdominal incision with the withdrawal of the forceps from the tunnel. The suture is then tied to the silastic tubing which is pulled cephaled by gentle traction until it is delivered to the neck.

There are a number of disadvantages to this technique. More trauma is caused to the patient by repeated passage through the subcutaneous tunnel between the incisions in the abdomen and neck. Further, there is always a chance that the suture or the slender forceps may break while making the subcutaneous tunnel. Furthermore, a substantial amount of time is required for delivery by this rior art technique of the silastic tube from an incision in the abdomen to an incision in the neck, which time delay may be an important factor due to the poor condition of the patients undergoing this procedure.

SHORT DESCRIPTION OF THE INVENTION

Accordingly, it is the principal object of the present invention to provide an improved technique and instrument for relaying silastic tubing or vascular graft subcutaneously between incisions in different parts of a living body, more specifically for performing what is known as a peritoneovenous shunt, or alternatively, in passing the tube while inserting a Hickman or Tenckhoff catheter or passing a vascular graft in performing an arterial bypass. Another object is to reduce the trauma to the patient caused by the foregoing procedure by reducing the time required therefor, and by reducing the number of required subcutaneous passages. A further object of the invention is to reduce the changes of mishaps occurring during the undertaking of the described procedures.

These and other objects are realized in accordance with the present invention in undertaking a subcutaneous placement of a tubular structure between incisions in different parts of the body, for example, a peritoneovenous shunt may be performed from an incision in the peritoneal cavity to an incision in the neck, by means of a surgical instrument comprising a relay rod of approved rigid surgical material, of generally cylindrical form, say, ¼ inch in diameter, which includes near the tip of its head, perpendicular to its axis, a bore large enough to accommodate the threading through of a silastic tube or vascular graft having an outer diameter of, say, ⅛ inch. A pair of longitudinal, colinear shallow grooves, extend parallel to the axis of the rod on opposite sides, distal to the bore. Near the upper and lower ends of the longitudinal grooves are respectively disposed a pair of shallow peripheral grooves, in planes normal to the axis of the rod. Distal to the longitudinal grooves in the relay rod head is a shaft portion, in coaxial relation, beyond which extends a handle having a plurality of fine longitudinal grooves or striations to provide a firm grip.

A modified form of the invention may include a relay rod, in which the distal portion of the head is, say, ⅜ inch in diameter, expanding to ⅝ inch forming a tear-shaped tip which terminates in a point. This embodiment includes a single groove, having a radius of, say, ⅜ inch, and extending parallel to the axis of the head from a bore near the tip to the proximal end of the handle.

It will be understood that in certain embodiments it may be convenient to have a curved handle.

In accordance with the procedure of the present invention, an end of a silastic tube or vascular graft is threaded through the bore, and then interposed into one or more elongated grooves parallel to the axis on the side of the head of the relay rod, where it is secured in place by two ties of heavy suture which are tied around the rod at the upper and lower peripheral grooves to hold the end portion of the silastic tube or graft in place on the rod and prevent it from rolling during the subcutaneous passage.

The rod with the silastic tube or vascular graft secured thereto is then passed subcutaneously between two incisions in the body, for example, from an abdominal incision to a neck incision, in performance of a peritoneovenous shunt. At the end of the traverse, the ties securing the silastic tube or graft on the relay rod are removed, disengaging the silastic tube; and the relay rod is removed from the subcutaneous tunnel.

The advantages over the prior art of the technique and instrument disclosed in accordance with the present invention are:

(a) the trauma caused by repeated passages through the subcutaneous tunnel is decreased;
(b) chances of mishaps which may result from the breaking of the tie or slender forceps during passage through the subcutaneous tunnel are substantially eliminated; and
(c) the time needed for completing passage of the silastic tube through a subcutaneous tunnel is substantially decreased, with particular benefit to patients in poor physical condition.

These, and other objects, features and advantages will be described in greater detail hereinafter with reference to the attached drawings.

SHORT DESCRIPTION OF THE DRAWINGS

DETAILED DESCRIPTION OF THE INVENTION

Figure 1:
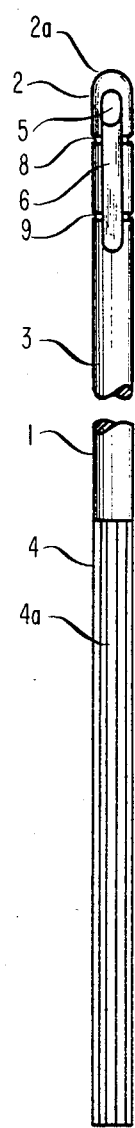
FIG. 1 is a side elevational showing of one embodiment of the relay rod of the present invention, rounded at the proximal end.
Figure 2:
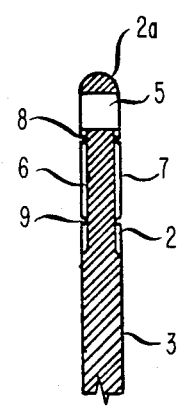
FIG. 2 is a sectional showing of the head and part of the shaft of the relay rod of FIG. 1, rotated 90° about its axis from the position shown in FIG. 1.
Figure 3:
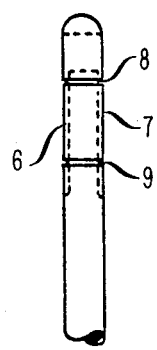
FIG. 3 is a showing, in side elevation, of the head and part of the shaft, as indicated in FIG. 2.
Figure 4:
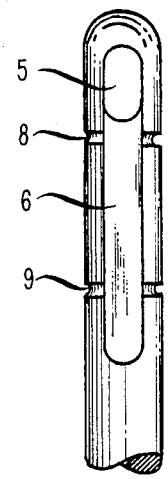
FIG. 4 is en enlarged showing, in side elevation, of the head of FIG. 1.

The surgical tube relay rod of the present invention comprises a rigid rod of approved surgical material, such as, for example, stainless steel, which is ¼ inch in diameter. It has three parts, comprising a head 2, a shaft 3, and a handle 4, all of which are integrally aligned to form a single cylindrical rod, which may be, for example, 20 inches long. In the embodiment under description, the head 2 is formed with a rounded tip 2a of ⅛ inch radius. Centered at a distance of ¼ inch from the tip 2a, is the tube receptor bore 5 which is ⅛ inch in diameter and ¼ inch along the rod axis, being semi-cylindrical, terminating in a curved surface of ⅛ inch radius at its upper and lower ends. This is drilled through the thickness of the rod, normal to its principal axis. Bore 5 is designed to accommodate the tube to be placed subcutaneously. On opposite sides of the rod 1, and commencing at the lower periphery of bore 5 are a pair of elongated grooves 6 and 7, each of which is ⅛ inch wide and extends 13/16 inch parallel to the axis. These grooves 6 and 7 function to prevent the tube 10 from rolling during use. In horizontal planes spaced at distances respectively ¼ and ¾ inch along the length of the tube relay rod 1, are a pair of circumferential grooves 8 and 9, each 1/32 inch wide and 1/32 inch deep, which grooves function to accommodate ties which secure the tube on the head 2 of rod 1.

Distal to lower ends of the longitudinal grooves 6 and 7, and at a distance of 1-3/16 inches from the tip 2a, is the upper end of the shaft 3 which extends in a distal axial direction a distance of 14-13/16 inches.

The handle 4 starts at a distance of 16 inches from the tip 2a of the silastic tube relay rod 1, and extends 4 inches in an axial direction. The handle 4 has a plurality of longitudinal grooves or striations, 4a, say, 1/64 inch deep, extending parallel to the axis, which are symmetrically spaced-apart around the cylindrical periphery, and which function to facilitate a firm grip on the instrument by the user.

METHOD OF OPERATION

It is contemplated that the pre-operative and preliminary operative procedures as to the treating and placement of the patient, making of the incisions, etc. will be carried out substantially with the current acceptable methods of surgical practice, for example, as described in the section entitled "Surgical Procedure" beginning on page 30 of the booklet entitled *Current Problems in Surgery*, Vol. XVI, No. 2, February 1979, Ascites: Its Correction By Peritoneovenous Shunting, supra.

Instead of using a slender bronchial alligator forceps or other prior art device, such as a straight rectal biopsy forceps, for passing the tube subcutaneously in the patient when performing a peritoneo-jugular shunt or an arterial bypass procedure, the technique in accordance with the present invention will rely on the use of the tube relay rod of the present invention which has been described in the preceeding paragraphs.

Figure 5A:
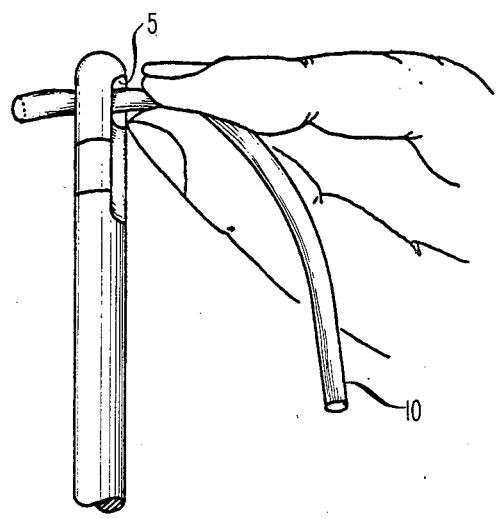
FIGS. 5A, 5B and 5C show the silastic tube threaded into and secured in place in the head of a relay rod of the present invention in the form of FIG. 1.
Figure 5B:
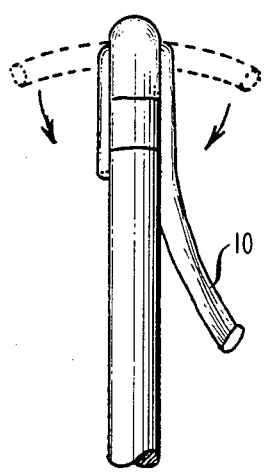
Figure 5C:
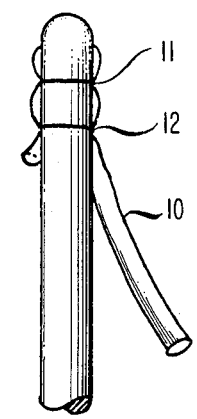

The tube relay rod 1 of the present invention is used, for example, as follows. A silastic tube 10 is passed through the receptor bore 5 of the rod 1 and secured in place in the longitudinal grooves 6 and 7 by a pair of heavy ties 11 and 12, of gut or heavy silk, which fit into the circumferential grooves 8 and 9 as shown in FIG. 5 of the drawings. The rod 1, carrying the silastic tube 10, is then passed subcutaneously from an abdominal incision in the patient to a neck incision, as illustrated diagrammatically in FIG. 6A and 6B.

The ties 11 and 12 securing the silastic tube 10 on tube relay rod 1 are then removed, and tube 10 is disengaged from rod 1, and the latter is withdrawn from the subcutaneous tunnel which has been formed in the patient by passage of the tube relay rod 1.

Figure 6A:
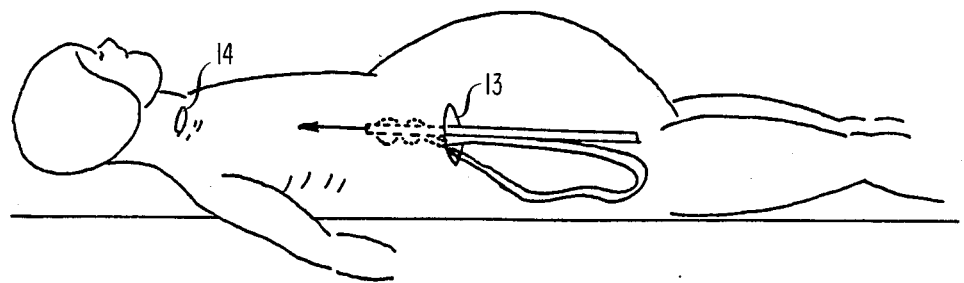
FIGS. 6A and 6B show successive steps in which the relay rod of the present invention including the silastic tube, is disposed in working relation to the patient during subcutaneous traverse.
Figure 6B:
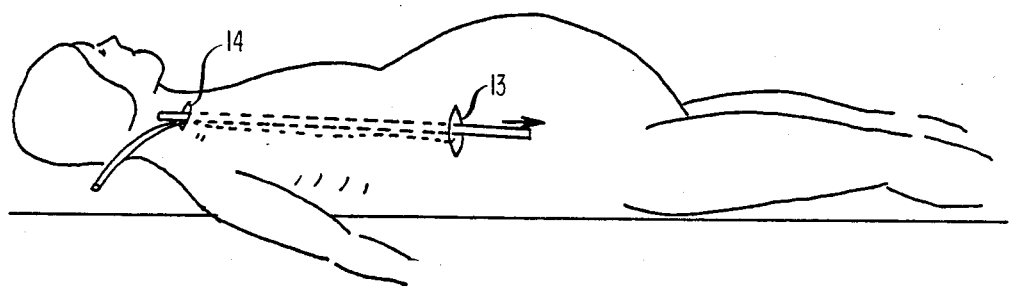

It will be understood that the purpose of the tube relay rod 1 of the present invention is to thread a silastic tube subcutaneously as illustrated in FIGS. 6A, 6B from a surgical incision in one area of the body such as abdominal incision 13, and a surgical incision in another area of the body, such as neck incision 14. More specifically, it can be used to pass a silastic tube in the peritoneovenous shunt, or for passing a silastic tube while inserting a Hickman or Tenckhoff catheter, or for passing a vascular graft in performing an arterial bypass procedure.

Figure 7A:
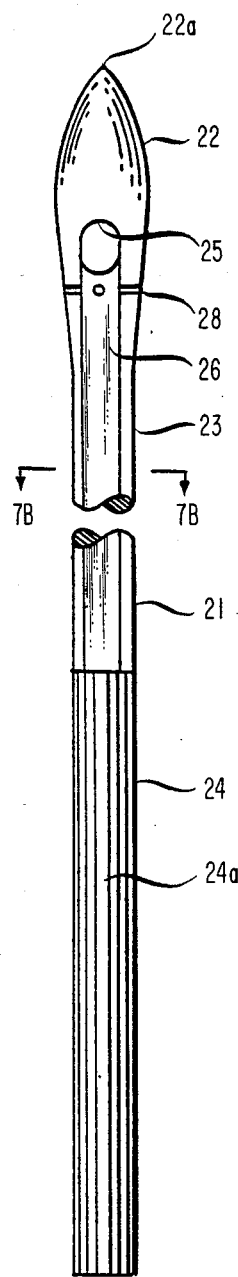
FIG. 7A shows, in side elevation, a modified form of the tube relay of the present invention, tearshaped at the proximal end.
Figure 7B:
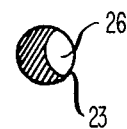
FIG. 7B is a showing of the head of FIG. 7A through a sectional plane indicated by the arrows 7B—7B in FIG. 7A.

A modified form of the surgical tube relay rod of the present invention is shown in FIGS. 7A, 7B. This may consist essentially of any suitable surgical material, such as, for example, stainless steel, or other metals, or suitable non-toxic rigid plastic materials. Like the device shown in FIG. 1 et seq., this embodiment also has three parts, a head 22, a shaft 23 and handle 24, all of which are integrally aligned to form a single substantially cylindrical rod, although it will be understood that the handle 4 may be curved, if desired. The overall device 21, as presently described, may extend, for example, 23½ inches in overall length, the handle portion 24 being 4 inches long, the body portion from the top of the bore 25 to the head of handle 24 being 18½ inches along the axis, and the axial distance from the top of bore 25 to the rod tip 22a being 1 inch. In the present embodiment, the handle 24 is ⅜ inch in diameter, and is surfaced with a plurality of striations 24a, parallel to the axis, to facilitate gripping. The body portion 23 has a uniform diameter of ⅜ inch along its length to the base of head 22. The diameter of the latter is gradually increased from ⅜ inch at its base to a maximum of ⅝ inch at its midsection, which coincides with the upper periphery of the bore 25. The upper end of 22 is tapered along a radius of curvature of 1-13/32 inches forming a cusp 22a at its proximal end. The bore 25 is centered in and penetrates through the head, being ¼ inch across, and ⅜ inch along the axis, having a radius of curvature of ⅛ inch at its upper and lower periphery. Extending in a distal direction from the lower periphery of bore 25 to the top of handle 24 is a single groove 26, which is shown in section in FIG. 7B, having a radius of curvature of 3/16 inch. A groove 28 which is 1/16 inch deep surrounds the head 22, bounded by a plane ⅛ inch below the lower end of bore 25.

The embodiment of FIGS. 7A, 7B operates as a relay for silastic tube and the like, in a manner similar to that shown in FIG. 1, except for the fact that the end of the silastic tubing, after being pulled through the bore 25, is secured in the single groove 26 by a single tie of suture accommodated in the groove 28.

It will be understood that the invention is not limited to the specific form or dimensions of the instrument disclosed or the particular application described by way of illustration, but only by the scope of the appended claims.

What is claimed is:

1. An instrument for performing a subcutaneous shunt for carrying a silastic tube or vascular graft between incisions in two parts of a body, which comprises in combination:
    a relay rod of rigid non-toxic material comprising head, shaft and handle portions;
    said head portion having a receptor bore extending therethrough adjacent the unindented tip portion at the proximal end in a direction substantially normal to the principal axis of said head, said receptor bore constructed to accommodate said silastic tube or vascular graft in threaded-through relation;
    said relay rod having a portion of reduced circumference distal to said receptor bore, said portion of reduced circumference including one or more longitudinal depressions substantially parallel to the principal axis of said rod, constructed to accommodate said silastic tube or vascular graft in position parallel to the principal axis of said relay rod.

2. An instrument in accordance with claim 1 wherein said handle portion includes a series of longitudinal striations to provide gripping means.

3. An instrument in accordance with claim 1 wherein said portion of reduced circumference of said rod comprises one or more longitudinal grooves disposed distal to said receptor bore substantially parallel to the principal axis of said rod, said grooves constructed to accommodate one or more portions adjacent the end of said silastic tube or vascular graft in longitudinal relation substantially parallel to the principal axis of said relay rod; and
    one or more circumferential grooves disposed in one or more planes between the upper and lower ends of said one or more longitudinal grooves to accommodate one or more ties of suture for securing said silastic tube or vascular graft in position parallel to the principal axis or said relay rod.

4. An instrument in accordance with claim 3 wherein the unindented tip portion of said head is rounded at its proximal end, and said one or more longitudinal grooves comprise a pair of longitudinal grooves disposed distal to said receptor bore on opposite sides of the principal axis of said relay rod; and said one or more circumferential grooves comprise a pair of circumferential grooves disposed in planes near the upper and lower ends of said longitudinal grooves.

5. An instrument in accordance with claim 3 wherein the unindented tip portion of said head terminates in a curved section which is tapered at its proximal end to an axially-directed cusp; and wherein said one or more longitudinal grooves comprise a single groove disposed distal to said receptor bore; and said one or more circumferential grooves comprise a single circumferential groove disposed in a plane near the upper end of said longitudinal groove.

6. An instrument in accordance with claim 1 comprising a rod having an overall length within the range between 8 and 30 inches, and an outer diameter within the range ⅛ and ⅜ inch;
    wherein said receptor bore has a cross-sectional dimension in a plane normal to the axis within the range 1/16 and ½ inch, and an axial length within the range 1/16 and ½ inch; and
    wherein said handle portion is straight, having a length between 4 and 8 inches.

7. An instrument in accordance with claim 4 wherein said unindented tip portion has a semicircular section in an axial plane having a radius within the range 1/16 and ⅜ inch;
    said relay rod having a pair of substantially parallel, diametrically opposite longitudinal grooves, each having a length within the range ½ to 29⅝ inches; said longitudinal grooves being semicircular in section in a plane normal to the axis and having radii within the range 1/32 to ¼ inch; and
    wherein said circumferential grooves are semicircular in section in an axial plane, having radii within the range 1/64 to ¼ inch.

8. An instrument in accordance with claim 5 wherein the curved section of said tip portion in an axial plane has a radius of curvature between ¼ and 2 inches;
    said single longitudinal groove having a length within the range ½ and 29⅝ inches, and a semicircular section in a plane normal to the axis having a radius witin the range 1/32 and ¼ inch; and wherein said single circumferential groove surrounds a plane near the upper end of said longitudinal groove, and said circumferential groove has a circular section in an axial plane with a radius within the range 1/64 to ¼ inch.

9. The combination in accordance with claim 1 wherein said handle is curved.

10. The method of carrying and positioning subcutaneously silastic tubing or vascular graft between incisions in two parts of a body which comprises the steps of:

forming a relay rod of substantially rigid non-toxic material;
interposing a bore near the tip of said rod constructed to accommodate a silastic tube or vascular graft in threaded-through relation;
threading a silastic tube or vascular graft through the bore of said rod;
securing the end portions of said silastic tube or vascular graft against the lateral surface of said relay rod distal to said bore substantially parallel to the axis of said relay rod by one or more suture ties, tied circumferentially around said relay rod;
utilizing said relay rod to form a subcutaneous tunnel between a pair of incisions in said body;
simultaneously delivering said silastic tubing or vascular graft therethrough;
removing said ties securing said silastic tube or vascular graft to said relay rod; and
removing said relay rod from said subcutaneous tunnel.

* * * * *